United States Patent [19]
Pinkham

[11] Patent Number: 5,906,223
[45] Date of Patent: May 25, 1999

[54] CHROMATOGRAPHY VALVE ASSEMBLY

[75] Inventor: Louis V. Pinkham, Simi Valley, Calif.

[73] Assignee: ITT Industries, Inc., White Plains, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/715,286

[22] Filed: Sep. 16, 1996

[51] Int. Cl.[6] .................................................... F16K 11/20
[52] U.S. Cl. ........................................... 137/597; 137/884
[58] Field of Search .................................... 137/597, 884, 137/883, 271

[56] References Cited

U.S. PATENT DOCUMENTS

| | | | |
|---|---|---|---|
| 2,209,024 | 7/1940 | Jones | 137/597 |
| 2,331,133 | 10/1943 | Nardone | 137/597 |
| 2,804,879 | 9/1957 | Hanson | 137/597 |
| 3,195,726 | 7/1965 | Saurenman | 137/597 |
| 3,670,893 | 6/1972 | Seid . | |
| 3,744,376 | 7/1973 | Carpenter | 137/597 |
| 4,287,908 | 9/1981 | Storgard | 137/597 |
| 4,444,215 | 4/1984 | Zukausky | 137/597 |
| 4,596,426 | 6/1986 | Clapp | 137/597 |
| 4,655,095 | 4/1987 | Russo | 137/597 |
| 5,238,017 | 8/1993 | Andersson | 137/271 |
| 5,273,075 | 12/1993 | Skaer | 137/883 |
| 5,277,224 | 1/1994 | Hutton et al. | 137/597 |
| 5,386,472 | 6/1968 | Szonntagh | 137/597 |
| 5,427,150 | 6/1995 | Skaer | 137/883 |

*Primary Examiner*—Denise L. Ferensic
*Assistant Examiner*—Ramyar Farid
*Attorney, Agent, or Firm*—Menotti J. Lombardi

[57] ABSTRACT

A unitarily formed diverter valve assembly for use in liquid chromatography. The valve assembly comprises a plurality of inlet and outlet ports, diverter valve systems, chambers, and a tortuous network of passageways all of which are arranged to accommodate the flow of fluids in a liquid chromatography system. The valve assembly is configured so as to direct the flow of fluid coming from an inlet port through the valve body where it can then be reversibly directed into or out of a chromatography column. On returning from the column, the fluid reenters the valve assembly where it is directed to an outlet port in order to exit the system. The valve assembly can also be configured so as to bypass the column altogether. Since the entire valve assembly is machined out of a single block of material having smooth liquid passageways, and since all flow compartments are shared and fully flushed when a flow-through valve is opened, dead-legs are virtually eliminated from the system.

16 Claims, 5 Drawing Sheets

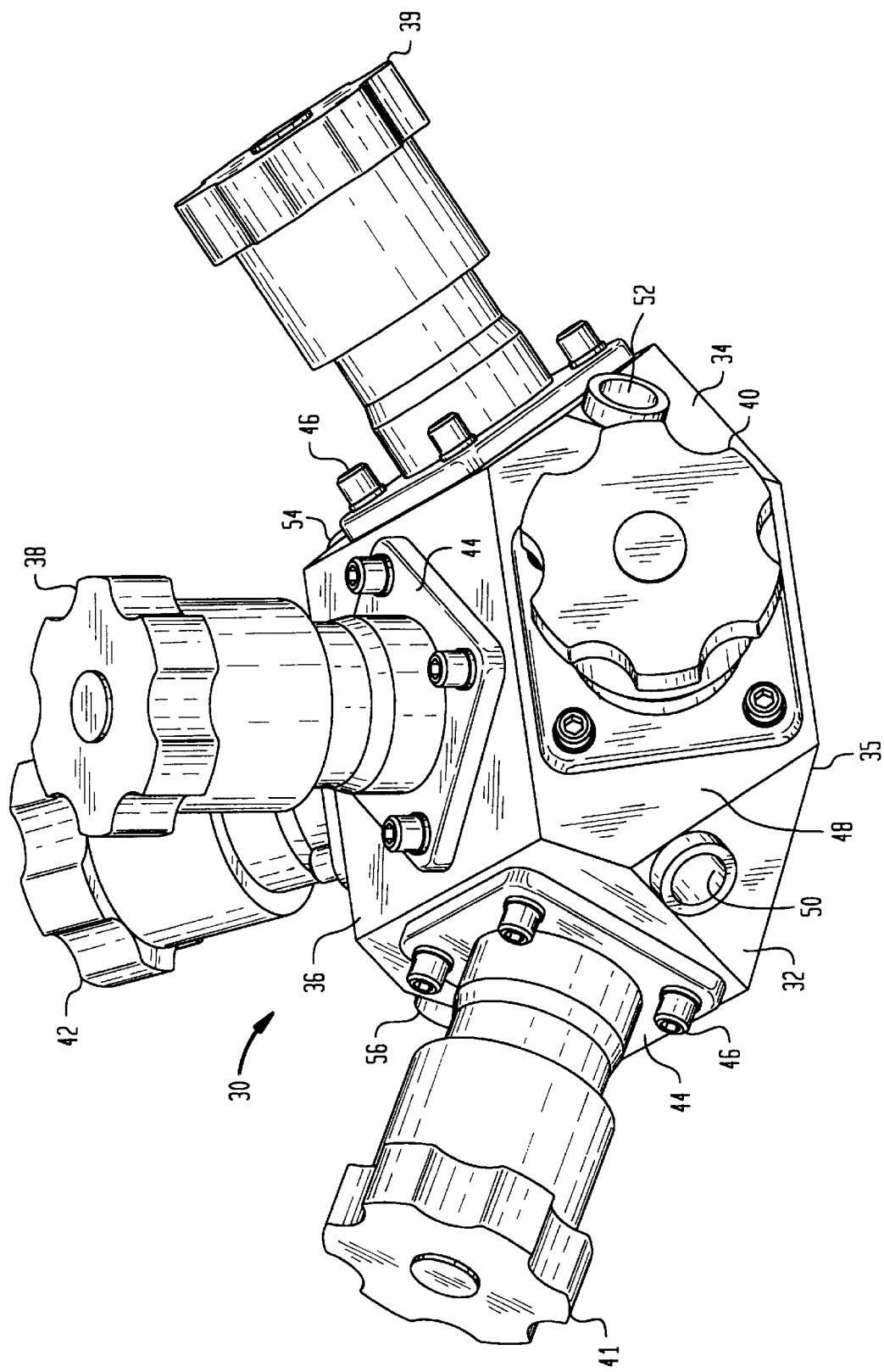

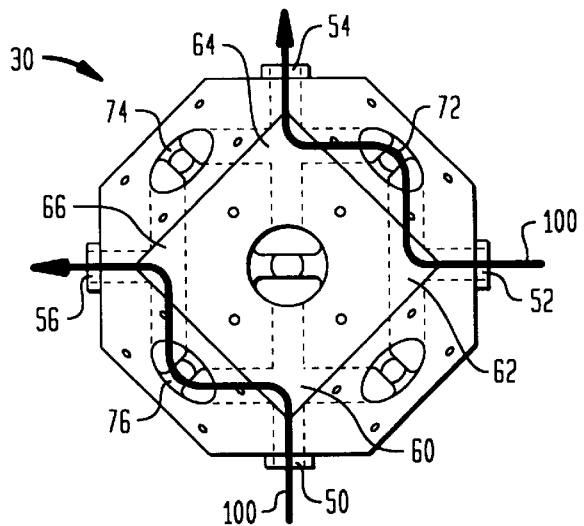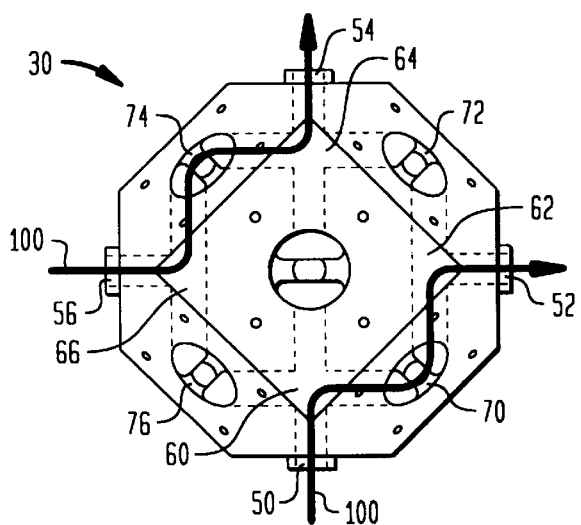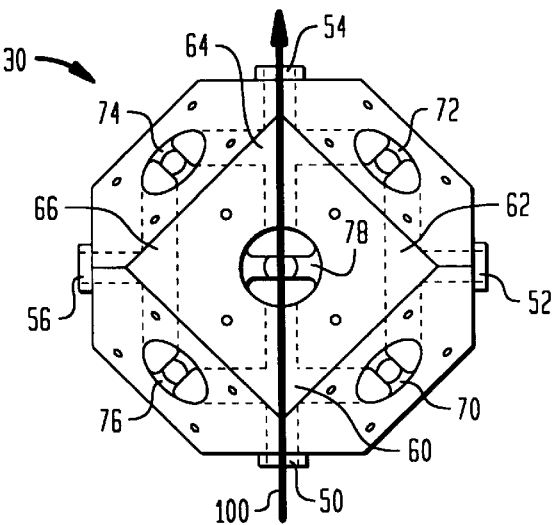

CHROMATOGRAPHY VALVE ASSEMBLY

FIELD OF INVENTION

The present invention relates to diverter type valves and more particularly to a diverter valve assembly designed for use in liquid chromatography.

BACKGROUND OF THE INVENTION

Only about 15% of the known compounds lend themselves to analysis by gas chromatography owing to insufficient volatility or thermal instability. Liquid column chromatography, on the other hand, does not have these limitations. The interchange or combination of solvents can provide special selectivity effects that are absent when the mobile phase is a gas. Ionic compounds, labile naturally occurring compounds, polymers, and high molecular weight polyfunctional compounds are conveniently analyzed by liquid chromatography. While liquid flow in traditional liquid chromatography was achieved by gravity, modern liquid column chromatography uses high pressure pumps with relatively short narrow-bore columns containing small particles of packing.

One of the most important parts in a liquid chromatography setup is the solvent delivery system. Such a system must be able to precisely deliver a solvent (or a mixture of different solvents) over a relatively broad flow range. Sampling valves are essential components of this solvent delivery system, allowing the sample to be reproducibly introduced into the column without significant interruption of the flow. Sampling valves are also used for connecting and disconnecting the chromatography column to the process piping (e.g., for flushing purposes).

An exemplary prior art liquid chromatography valve setup is schematically depicted in FIGS. 1A–1D. FIG. 1A shows a valve assembly 10 comprising valves 12a, 12b, 14a, 14b, 16a, and 16b. Liquid enters the system from the entrance process piping 20 and can be directed through the valve assembly 10 by controlling the afore-mentioned valves as will be later explained. The system gives the user the flexibility to have the product fluid flow through a chromatography column (not shown) in a forward (FIG. 1B) or reverse (FIG. 1C) direction, or the product fluid can be made to completely bypass the column (FIG. 1D). Liquid leaves the valve assembly through the exit process piping 22.

Fluid can flow through the prior art valve assembly 10 depicted in FIG. 1A in any one of the three directions depicted in FIGS. 1B–1D. The fluid flow is represented by arrows 25 in these figures. In FIG. 1B, which represents the forward product flow through the column, valve 14a is opened allowing the fluid to flow from the process piping into the valve assembly 10. Valve 16a is also opened allowing the fluid to flow into the chromatography column (not shown). The fluid returns from the chromatography column passing through valve 16b and reentering the valve assembly. The fluid leaves the valve assembly passing through valve 14b on its path back to the process piping. Valves 12a and 12b remain closed during this process. According to the reverse process flow depicted in FIG. 1C, fluid entering the valve assembly 10 from the process piping can flow through valves 12a and 16b into the column, returning from the column through valve 16a, and exiting the valve assembly through valve 12a back through the process piping. Valves 14a and 14b remain closed during this process. The column may be bypassed altogether according to the process flow depicted in FIG. 1D, where the liquid entering into the valve assembly from the process piping encounters opened valves 12a, 14a, 12b and 14b, exiting the valve assembly without entering the chromatography column which remains inaccessible by closing valves 16a and 16b.

Prior art liquid chromatography valve assemblies like the one described above are typically fabricated using either six independent valves or two two-way diverter valves with two independent valves, connected either by sanitary tri-clams or welded to tee fittings. The problem encountered with these systems, which is especially prevalent in those using the tee fittings, is the existence of dead-legs. Dead-legs are areas of liquid that have become trapped in the valve assembly when the flow of liquid in a particular branch of the system is halted. In dead-legs, fluid can stagnate causing contaminants to accumulate or micro-organisms to grow. This presents a serious problem in liquid chromatography where such contaminants can adversely affect the results of a particular analysis. Hence the need for a diverter type valve assembly in which all flow compartments are shared and fully flushed when a flow through valve is opened clearly exists.

Diverter valves are not particularly new, and, in fact, the prior art includes many examples of different types of these valves. An example of such a valve is described in U.S. Pat. No. 5,273,075 to R. A. Skaer entitled DIVERTER VALVE. The valve described in this patent comprises a diaphragm type valve with a single inlet port and two outlet ports, and is set up such that the flow of fluids can be directed from the inlet port to one or the other outlet ports. The valve operates by closing a diaphragm against an edge or weir of a partition with the valve housing which prohibits fluid flow to the one port while accommodating flow to the other port. This specific diverter valve is made for use with systems that require only a single inlet port and no more than two outlet ports, and hence, such a valve system would not accommodate the intricate plumbing necessary to operate a liquid chromatography system. Moreover, the valve assembly described above requires specialized components, including a specific housing that itself is the subject of a U.S. patent (U.S. Pat. No. 5,427,150 to Skaer et al. Entitled HOUSING FOR A DIVERTER VALVE).

The problem with most prior art diverter valve assemblies revolves around the fact that they are not manufactured out of a single block of material. These valve assemblies are therefore relatively expensive to manufacture, and are, in general, difficult to clean in place due to the dead-legs present when tee fittings are used in them. When these valves are fully assembled, they also take up a large volume in space requiring more installation volume. Since it is the object of most bio technology and pharmaceutical firms to minimize dead-legs and to make process piping and valve assemblies as compact as possible, a new valve assembly which ameliorates these difficulties is sorely needed.

It is therefore an object of the present invention to provide a compact unitarily formed diverter type valve system for use in liquid chromatography in which dead-legs between the valves are eliminated and in which the installation space needed for the system is minimized.

SUMMARY OF THE INVENTION

A unitarily formed diverter valve assembly for use in liquid chromatography. The valve assembly is configured so as to direct the flow of fluid coming from an inlet port through the valve body where it can then be reversibly directed into and out of a chromatography column. On returning from the column, the fluid reenters the valve assembly where it is directed to an outlet port in order to exit the system. The valve assembly can also be configured so as to bypass the column altogether. The smooth and tortuous network of passageways in the valve body, in combination with the placement and operation of the diverter valves, substantially eliminates dead-legs from the system.

BRIEF DESCRIPTION OF THE DRAWINGS

For a detailed understanding of the present invention, reference should be made to the following detailed description taken in conjunction with the accompanying drawings wherein:

FIG. 2 is a perspective view of the instant invention valve assembly;

FIGS. 4A–4C are schematic views of the instant invention valve assembly showing possible product flow directions.

DETAILED DESCRIPTION OF THE INVENTION

Figure 1A:
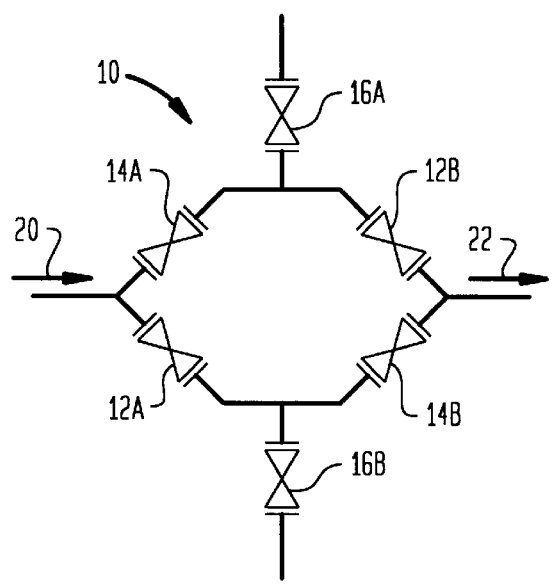
FIGS. 1A–1D are schematic views of a prior art chromatography valve assembly showing possible product flow directions.
Figure 1B:
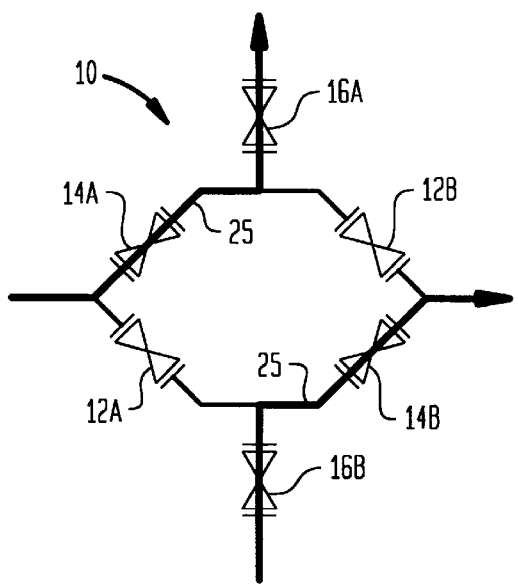
Figure 1C:
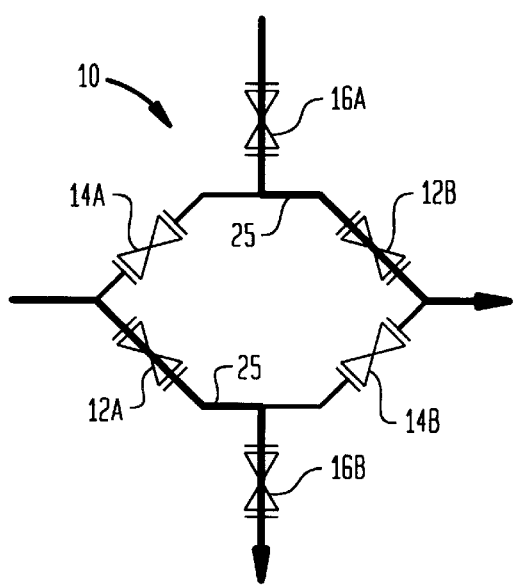
Figure 1D:
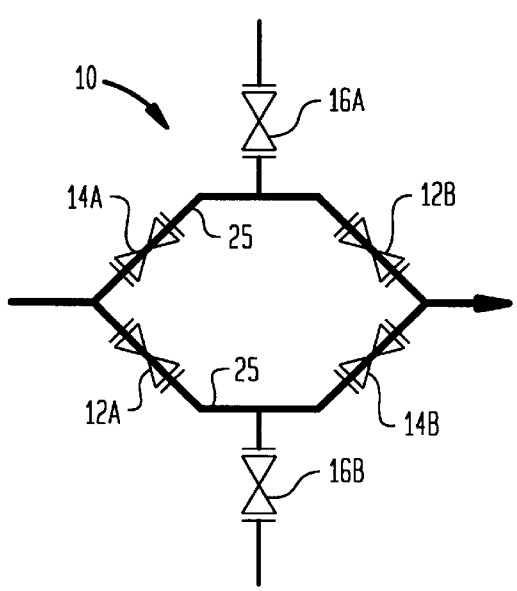

Referring to FIG. 2, there is shown a perspective view of the instant invention chromatography valve assembly 30. The valve assembly 30 comprises a unitarily formed valve body 32, which may be cast or machined from iron, bronze, stainless steel or aluminum, or may be molded from a suitable plastic or plastic composite material. The outer body 32 is generally that of an octahedral pyramid having a octagonal base 34, a square top surface 36, and a combination of triangular 35 and distorted hexagonal 48 side faces. The top square surface 36 is planar and mounted thereon is the first of five manual bonnet assemblies 38,39,40,41,42 for manually controlling the operation of the underlying valves. The operation of manual bonnets in diverter valve assemblies is well known to those skilled in the art, and is explained, for example, in afore-described U.S. Pat. No. 5,273,075, the specification of which is incorporated herein by reference. It should be noted that although manual bonnet assemblies are shown, other means such as pneumatic or electrical actuators may be mounted on the outer valve body in order to control the valves, thereby eliminating the need for the manual bonnets. The manual bonnets as shown are affixed to the valve body via plates 44, each plate having four suitable screw-type fasteners 46. Extending downwardly and outwardly from each edge of the top square surface 36 of the valve body 32 is a distorted hexagonal side face 48, each side face being planar and having a manual bonnet mounted thereon. These side faces are angled at approximately 30° with respect to the octagonal base of the valve body. The reason for the particular angled mounting of the additional four bonnet assemblies 39,40,41,42 has to do with valve drainage concerns, and will also be explained in detail later.

Still referring to FIG. 2, inlet/outlet ports 50, 52, 54, 56 are located on the triangular side faces 35 of the valve body 32, each port being located between two manual bonnet assemblies. The triangular faces 35 rise perpendicularly from the octagonal base of the valve body, and each triangular face is located approximately 90° from the other. The ports may be threaded, flanged, or left smooth for welding, depending on the desired coupling to the process piping.

Figure 3A:
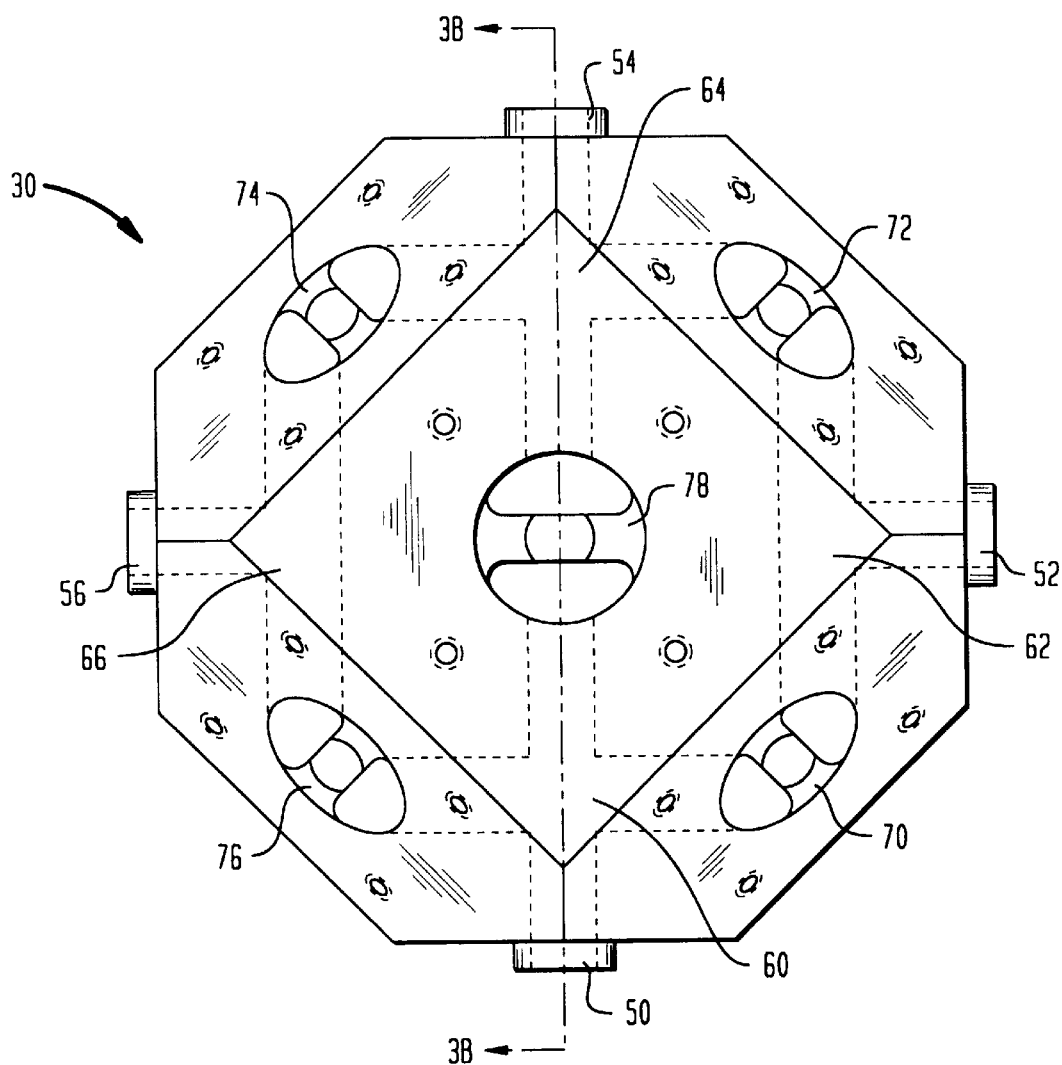
FIG. 3A is a top view of the valve assembly of the instant invention without the manual bonnets.

Referring now to FIG. 3A, there is shown a top view of the valve assembly, minus the manual bonnets and with a partial cross-sectional view of the underlying channel network drawn in with broken lines. As can be seen in this figure, ports 50, 52, 54 and 56 are arranged at angles of approximately 90° with respect to each other on opposing ends of the octagonal base section of the valve assembly. Each port opens into a chamber in the valve assembly 30—port 50 opening into chamber 60, port 52 opening into chamber 62, port 54 opening into chamber 64, and port 56 opening into chamber 66. Fluid entering any of the ports encounters a chamber and channels leading to three diverter valves. Fluid entering port 50, for example, encounters chamber 60 and channels leading to diverter valves 70, 76 and 78. The smooth and tortuous network of passageways that lead through the valve assembly connect the ports with the chambers and valves in a such a way that the valve assembly is fully drainable as will be later explained. The flow of the fluid is controlled by the diverter valves 70,72, 74,76,78 and may be adjusted to permit specific flow directions which, in combination with the smooth and tortuous passageways, eliminate dead-legs from the system.

Figure 3B:
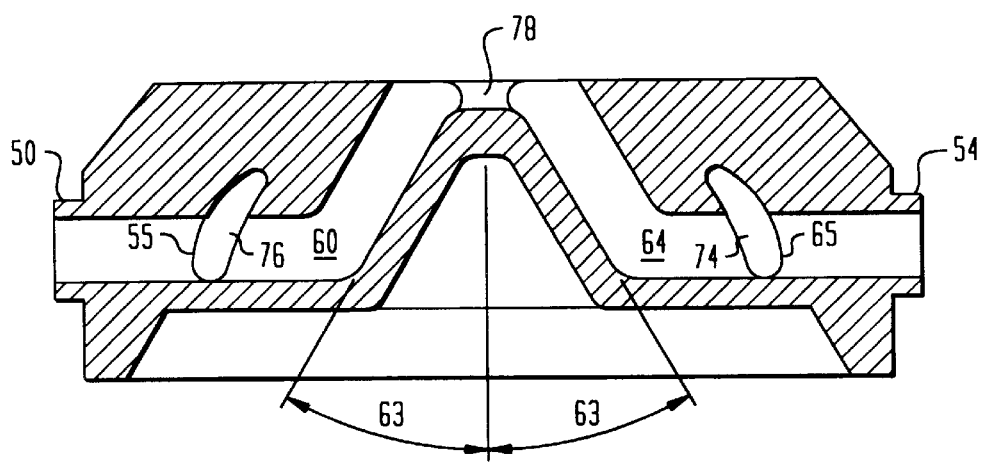
FIG. 3B is an enlarged cross-sectional view through line A—A of FIG. 3A.

Referring now to FIG. 3B, there is shown an enlarged cross-sectional view of the valve assembly through line A—A of FIG. 3A. As can be seen in the figure, port 50 opens into chamber 60. A passageway 55 leading to diverter valve 76 can also be seen in this figure. Chamber 60 is connected to chamber 64 via diverter valve 78. The passageway that connects these two chambers is inclined, rising sharply before encountering diverter valve 78 and then falling sharply after encountering the valve. The angle of inclination 63 measured from either side of the diverter valve 78 is approximately 30°. In chamber 64, a passageway 65 leading to diverter valve 74 can be seen. Finally in this figure, port 54 can be seen as opening into chamber 64.

Figure 3C:
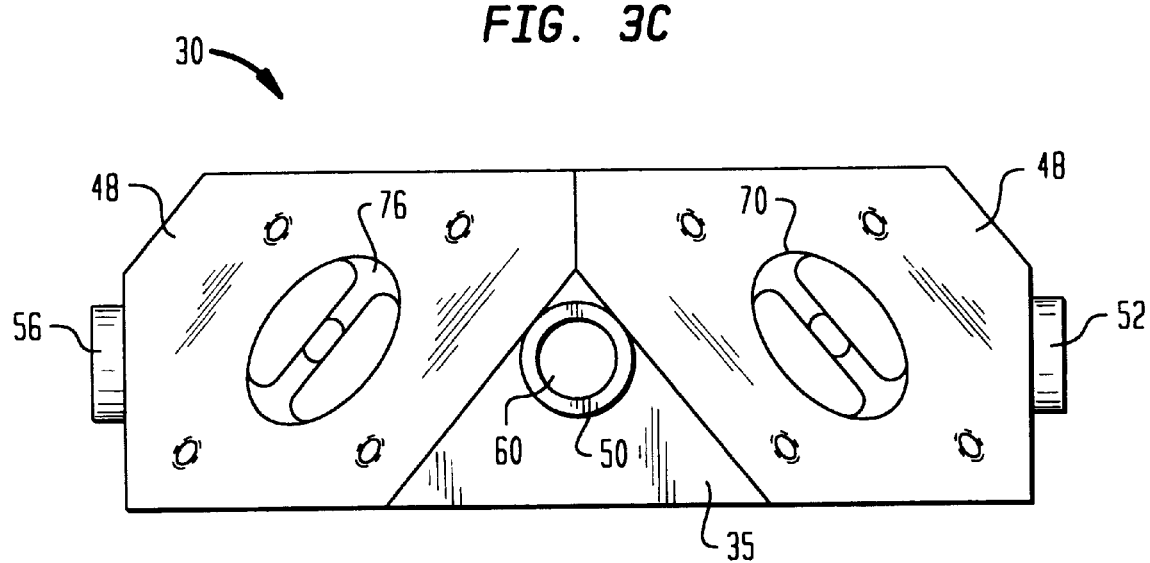
FIG. 3C is an enlarged side elevational view of the instant invention valve assembly without the manual bonnets.

Referring now to FIG. 3C, there is shown an enlarged side elevational view of the instant invention valve assembly 30. This particular side elevational view is directed down port 50 which is disposed on triangular surface 35. As explained above, port 50 opens into chamber 60 which is connected by channels to diverter valves 70, 76 and 78. In this figure, diverter valves 70 and 76 can be seen on opposite sides of port 50, being disposed beneath the afore-described distorted hexagonal side faces 48. These diverter valves, as well as diverter valves 72 and 74 (not shown in this figure), are machined in the position of their drain angle which is approximately 30° as measured from the octagonal base of the valve assembly. This arrangement, coupled with the fact that valve 78 (as seen in FIG. 3B) is at a high point in the valve assembly, allows the valve assembly 30 to be fully and easily drainable. Ports 56 and 52 are also clearly visible in this figure.

Figure 3D:
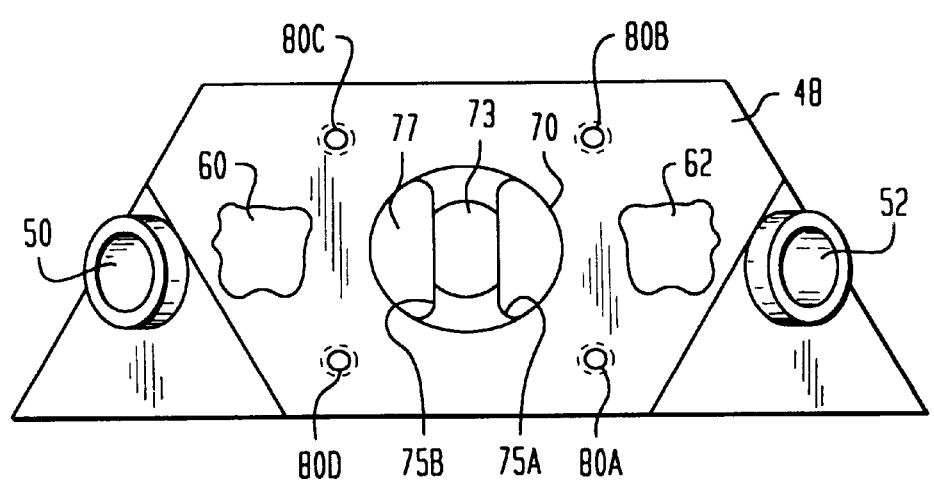
FIG. 3D is an enlarged side elevational view of the instant invention valve assembly rotated approximately 45° from the view depicted in FIG. 3C.

Referring now to FIG. 3D, there is shown an enlarged side elevational view of the valve assembly 30 rotated approximately 45° from the view depicted in FIG. 3C. The diverter valve 70 comprises a valve body having a substantially flat, distorted hexagonal side face 48 and a centrally positioned opening 71 which is bisected by a weir 73. Looking directly into diverter valve 70, one surface 75a of the valve body is curved to form a channel connected to port 52, while the other surface 75b is curved to form a channel connected to port 50. The smooth unobstructed chamber 77 and channel through this valve (not shown) permit flow of fluids which, for example, may enter port 50, pass through chamber 60, go across valve 70, pass into chamber 62, and exit port 52. The holes 80*a,* 80*b,* 80*c* and 80*d* in side face 48 are for locating mounting bolts or suitable fasteners therethrough. It should be understood that the components described for diverter valve 70 are repeated for each of the other four diverter valves in the valve assembly.

Possible fluid flow paths in the valve assembly of the instant invention are depicted in FIGS. 4A–4C. In the preferred embodiment described below, port 50 is connected to an inlet process piping system (not shown) and functions as an inlet port. Port 54 is connected to an outlet process piping system (not shown) and functions as an outlet port. Ports 52 and 56 are connected to a chromatography column (not shown) and function as either inlet or outlet ports to this column depending on the direction of fluid flow. The flow in these figures is represented by arrows 100.

Referring now to FIG. 4A, fluid, containing the product or products to be analyzed, flows from the process piping in a forward direction through port 50, into chamber 60, across valve 76, into chamber 66, and out port 56 to a chromatography column. The fluid returns from the chromatography column entering the valve assembly through port 52, into chamber 62, across valve 72, into chamber 64, and out of the assembly to the outlet process piping through port 54. Since chambers 60, 62, 64 and 66 are common to two valves respectively (72 and 76), the fluid being piped through each port (50, 52, 54, 56) will flush and sweep through the chamber preventing stagnation and the opportunity for contaminants or particulates to accumulate and/or growth of microorganisms to develop.

Referring now to FIG. 4B, there is shown the product flow through the chromatography valve assembly in a reverse direction with respect to the flow depicted in FIG. 4A. Product here flows from the inlet process piping into the valve assembly 30 via port 50, into chamber 60, across valve 70, into chamber 62, and out port 52 into a chromatography column. Product returns from the chromatography column entering the valve assembly 30 through port 56, into chamber 66, across valve 74, into chamber 64, and out to the outlet process piping through port 54. As in the case where the fluid is flowing in a forward direction, chambers 60, 62, 64 and 66 are common to two valves respectively (this time 70 and 74), and the fluid being piped through each port (50, 52, 54, 56) will flush and sweep through the chamber preventing stagnation and the opportunity for contaminants or particulates to accumulate and/or growth of microorganisms to develop.

The chromatography column may be bypassed altogether as is depicted in FIG. 4C. According to this process flow, liquid enters the valve assembly 30 through port 50 and passes into chamber 60. The fluid then crosses valve 78 and passes into chamber 64. From chamber 64 the fluid exits the valve assembly 30 through port 54. During the column bypassing process, valves 70, 72, 74 and 76 remain closed, and fluid remaining in chambers 62 and 66 (as well as in the column) remains undisturbed in the process.

The valve assembly 30 described herein is simple and easy to use, and represents an improvement over prior art diverter valve assemblies. The device is machined out of one block of material, and all flow compartments are shared and fully flushed when a flow through valve is opened, thereby eliminating dead-legs. The main body of the valve assembly (not including any manual bonnets) has an overall diameter of less than 4 inches with a height of less than 1½ inches and internal piping diameters on the order of ½ inch, all of which make the instant device much more compact than the five or six independent valve assemblies of the prior art, thereby minimizing installation space. The afore-mentioned dimensions also make the valve assembly 30 easy to hold and assemble to a liquid chromatography system. In addition, the ½ inch diameter of the internal network of passageways and inlet/outlet ports is compatible with common liquid chromatography tubing dimensions. It should be understood, however, that the valve assembly and representative passageways can be manufactured in any size required. While the valve assembly 30 described herein is especially suited for use in liquid chromatography, it should also be understood that the device can be adapted for other uses as desired. It should further be understood that the embodiments described herein are merely exemplary and that a person skilled in the art may make many variations and modifications to the embodiments utilizing functionally equivalent elements to those described herein. Any and all such variations or modifications as well as others which may become apparent to those skilled in the art, are intended to be included within the scope of the invention as defined by the appended claims.

What is claimed is:

1. A unitarily formed diverter valve assembly for diverting the flow of fluids in a liquid chromatography system comprising;

a valve body;

first, second, third, and fourth ports;

first, second, third and fourth chambers; and first, second, third, fourth and fifth diverter valves;

wherein said first port is associated with said first chamber, said second port is associated with said second chamber, said third port is associated with said third chamber, and said fourth port is associated with said fourth chamber; and wherein said first diverter valve is disposed between said first and said second chamber such that a first side of said first diverter valve is positioned in said first chamber and a second side of said first diverter valve is positioned in said second chamber, said second diverter valve is disposed between said second and said third chamber such that a first side of said second diverter valve is positioned in said second chamber and a second side of said second diverter valve is positioned in said third chamber, said third diverter valve is disposed between said third and said fourth chamber such that a first side of said third diverter valve is positioned in said third chamber and a second side of said third diverter valve is positioned in said fourth chamber, said fourth diverter valve is disposed between said fourth and said first chamber such that a first side of said for diverter valve is positioned in said fourth chamber and a second side of said fourth diverter valve is positioned in said first chamber, and said fifth diverter valve is disposed between said first and said third chamber such that a first side of said fifth diverter valve is positioned in said first chamber and a second side of said fifth diverter valve is position and in said third chamber and wherein one of said first, second, third, fourth and fifth diverter valves is disposed at a predetermined highpoint in said valve body, relative to all other of said first, second, third, fourth and fifth diverter valves, and the other of said first, second, third, fourth and fifth diverter valves are disposed in said valve body at predetermined angles suitable for draining said valve assembly.

2. The diverter valve assembly of claim 1, wherein said valve body comprises an octahedral pyramid structure having:

a substantially planar, octagonally shaped base portion;

a substantially planar square top surface;

four distorted hexagonal side faces projecting downwardly from said square top surface; and, four triangular faces rising perpendicularly from said base portion, said triangular faces being disposed between said four side faces.

3. The diverter valve assembly of claim 2, wherein said ports are disposed on said triangular faces.

4. The diverter valve assembly of claim 3, wherein said plurality of ports is equal to four ports.

5. The diverter valve assembly of claim 1, wherein at least two of said ports are connected to opposite sides of a chromatography column.

6. The diverter assembly of claim 1, wherein said predetermined angles are approximately 30° with respect to a base of the diverter valve assembly.

7. The diverter valve assembly of claim 1, further comprising a plurality of manual bonnets, each of said manual bonnets corresponding to one of said diverter valves which is disposed thereunder.

8. The diverter valve assembly of claim 7, wherein said manual bonnets operate to manually control the operation of said diverter valves.

9. The diverter valve assembly of claim 1, wherein fluid flowing in a first direction enters said valve assembly through said first port, passes through said first chamber, is directed across said first diverter valve into said second chamber, exits said valve assembly through said second port, reenters said valve assembly through said fourth port, passes through said fourth chamber, is directed across said third diverter valve, passes through said third chamber, and exists said valve assembly through said third port.

10. The diverter valve assembly of claim 9, wherein said second diverter valve operates to prevent fluid communication between said second and said third chamber, said fourth diverter valve operates to prevent fluid communication between said fourth and said first chamber, and said fifth diverter valve operates to prevent fluid communication between said first and said third chamber.

11. The diverter valve assembly of claim 1, wherein fluid flowing in a second direction enters said valve assembly through said first port, passes through said first chamber, is directed across said fourth diverter valve into said fourth chamber, exits said valve assembly through said fourth port, reenters said valve assembly through said second port, passes through said second chamber, is directed across said second diverter valve, passes through said third chamber, and exists said valve assembly through said third port.

12. The diverter valve assembly of claim 11, wherein said first diverter valve operates to prevent fluid communication between said first and said second chamber, said third diverter valve operates to prevent fluid communication between said third and said fourth chamber, and said fifth diverter valve operates to prevent fluid communication between said first and said third chamber.

13. The diverter valve assembly of claim 1, wherein fluid flowing in a third direction enters said valve assembly through said first port, passes through said first chamber, is directed across said fifth diverter valve into said third chamber, and exits said valve assembly through said third port.

14. The diverter valve assembly of claim 13, wherein said first diverter valve operates to prevent fluid communication between said first and said second chamber, said second diverter valve operates to prevent fluid communication between third and said second chamber, said fourth diverter valve operates to prevent fluid communication between said third and said fourth chamber, and said fourth diverter valve operates to prevent fluid communication between said first and said fourth chamber.

15. The valve assembly of claim 1, wherein said second port and said fourth port are connected to opposite ends of a chromatography column.

16. A diverter valve assembly for use in liquid chromatography comprising:

a unitarily formed valve body comprising an octahedral pyramid structure having: a substantially planar, octagonally shaped base portion; a substantially planar square top surface; four distorted hexagonal side faces projecting downwardly from said square top surface; and four triangular faces rising perpendicularly from said base portion, said triangular faces being disposed between said four side faces;

a plurality of ports in said valve body, at least one of said plurality of ports functioning as an inlet port for allowing a liquid to enter into said valve body, at least one other of said plurality of ports functioning as an outlet port for allowing said liquid to exit said valve body, and at least two other of said plurality of ports each operable in a first inlet mode and a second outlet mode respectively, with respect to said valve body;

a plurality of chambers in said valve body, each one of said chambers being associated with one of said ports;

a tortuous network of channels communicating between said ports in said valve body for directing the flow of said liquid through said valve body; and, a plurality of diverter valves located in said valve body, said diverter valves operating to control the flow of said liquid in said valve body, one of said plurality of diverter valves disposed at a predetermined highpoint in said valve body, relative to all other of said plurality of diverter valves, and the other of said plurality of diverter valves disposed in said valve body at approximately 30° angles with respect to a base of the diverter valve assembly, suitable for draining said valve assembly, wherein actuation of a predetermined combination of said ports, chambers, channels and diverter valves produces a smooth and unobstructed path for said liquid which substantially eliminates dead-legs in said valve assembly.

* * * * *